United States Patent
Watanabe et al.

(10) Patent No.: US 7,048,901 B2
(45) Date of Patent: May 23, 2006

(54) ELECTRICAL CONNECTION STRUCTURE, PRODUCTION METHOD THEREOF, AND ELECTRIC WIRING METHOD

(75) Inventors: Hiroyuki Watanabe, Minamiashigara (JP); Chikara Manabe, Minamiashigara (JP); Taishi Shigematsu, Minamiashigara (JP); Kei Shimotani, Minamiashigara (JP); Masaaki Shimizu, Ashigarakami-gun (JP)

(73) Assignee: Fuji Xerox Co., Ltd., Tokyo (JP)

( * ) Notice: Subject to any disclaimer, the term of this patent is extended or adjusted under 35 U.S.C. 154(b) by 317 days.

(21) Appl. No.: 09/995,626

(22) Filed: Nov. 29, 2001

(65) Prior Publication Data

US 2002/0132500 A1   Sep. 19, 2002

(30) Foreign Application Priority Data

Mar. 16, 2001 (JP) ............................. 2001-075834

(51) Int. Cl.
 *C01B 31/00* (2006.01)
 *H01R 4/58* (2006.01)
(52) U.S. Cl. .................... 423/414; 439/87; 977/DIG. 1
(58) Field of Classification Search ................. 422/50, 422/68.1, 129; 435/4, 5, 6, 7.1; 536/25.3
See application file for complete search history.

(56) References Cited

U.S. PATENT DOCUMENTS 5,866,434 A * 2/1999 Massey et al. ............... 436/526
6,159,742 A   12/2000 Lieber et al.
6,362,011 B1 * 3/2002 Massey et al. ............... 436/526
6,576,341 B1 * 6/2003 Davey et al. ................. 428/376
2002/0172963 A1 * 11/2002 Kelley et al. ................... 435/6
2004/0081900 A1 * 4/2004 Bureau et al. .................. 430/31

FOREIGN PATENT DOCUMENTS

JP   A 2000-516708   12/2000

OTHER PUBLICATIONS

BIOCHEMISTRY, by Albert L. Lehninger [Published by Worth Publishers, Inc., 70 Fifth Avenue, New York, NY 10011] published in 1970, pp. 67-71.*
Danny Porath et al., "Direct measurement of electrical transport through DNA molecules", Nature, vol. 403, pp. 635-638, 2000.

* cited by examiner

*Primary Examiner*—Ardin H. Marschel
*Assistant Examiner*—Shubo (Joe) Zhou
(74) *Attorney, Agent, or Firm*—Oliff & Berridge PLC

(57) ABSTRACT

An electrical connection structure that is able to electrically connect wiring to a biopolymer, a production method of the electrical connection structure, and an electric wiring method which is able to perform wiring on a nanometer-scale. A first aspect of the production method of the present invention uses a carbon nanotube as an electrode, and makes the carbon nanotube contact the biopolymer. A second aspect of the production method applies electric current between the electrode and the biopolymer of the first aspect. The electrical connection structure of the present invention comprises at least the electrode formed by the carbon nanotube and the biopolymer, wherein the electrode is in contact with the biopolymer. In the electric wiring method of the present invention, the electrode formed by the carbon nanotube contacts the biopolymer to complete an electrical connection.

14 Claims, 5 Drawing Sheets

A: PROBE IS Au
B: PROBE IS A NANOTUBE
C: PROBE IS A NANOTUBE (AFTER APPLICATION OF VOLTAGE)

ELECTRODE: NANOTUBE
SAMPLE: DNA
1: BEFORE A VOLTAGE OF 15V IS APPLIED
2: AFTER A VOLTAGE OF 15V IS APPLIED

ELECTRICAL CONNECTION STRUCTURE, PRODUCTION METHOD THEREOF, AND ELECTRIC WIRING METHOD

BACKGROUND OF THE INVENTION

1. Field of the Invention

The present invention relates to an electrical connection structure, a production method thereof, and an electric wiring method. More specifically, the present invention relates to an electrical connection structure using a biopolymer such as DNA, RNA, or a protein, a production method of the electrical connection structure, and an electric wiring method.

2. Description of the Related Art

Heretofore, expectations that biopolymer insulating materials such as DNA, RNA, and proteins would be used as electronic components were low.

However, due to the development of techniques for manufacturing nanometer-scale devices, the uses of such biopolymers as electronic materials for manufacturing electronic devices began to be studied. Further, the use of these biopolymers is also expected in tests and inspections which connect electrodes to the biopolymers to measure their electric properties. The biggest problem in this case is electrical connection between the biopolymers and the electrodes. In a method of producing electrodes that are used in silicon devices and the like, they are generally wired (electrically connected) by forming a pattern on a photoresist with the light exposure method or the electron beam exposure method, and then depositing metals, semiconductors or the like on the pattern. Moreover, there is a method in which a thiol group (SH group) is intentionally added to a molecule, and the molecule having the thiol group added thereto is optionally adhered onto a gold electrode.

However, in methods in which the photoresist is used, the biopolymers, such as DNA, RNA, or a protein, are chemically damaged by an organic solvent or the like used in resist development. Even if the biopolymers are simply adhered onto a metal electrode, electric conductivity varies according to the adhering state of the biopolymers. In the method in which a thiol group is used, materials are limited, and most biopolymers cannot be used.

Further, when a biopolymer such as DNA, RNA, or a protein is simply placed onto a metal (such as gold or platinum) electrode, contact resistance between the metal electrode and the biopolymer is not constant due to the effects of an oxide film on the surface of the metal Therefore, a stable electrical connection cannot be expected, and the contact resistance value deviates by about 10% or more.

Furthermore, many of the biopolymers such as DNA, RNA, and proteins are insulating materials having a resistance of 5 MΩ·cm or more. When such biopolymers are used as electronic elements, nanometer-scale electrodes need to be formed and disposed so as to be close to the biopolymer. However, since the size of metal wiring is too large (too thick) relative to the size of the biopolymer, it has been difficult to form minute electric wiring.

SUMMARY OF THE INVENTION

An object of the present invention is to provide an electrical connection structure enabling electric wiring which electrically connects to a biopolymer such as DNA, RNA, or a protein in an efficient manner, and a production method of the electrical connection structure. Another object of the present invention is to provide an electric wiring method which enables nanometer-scale electric wiring.

The above objects are achieved by the following means.

A first aspect of the production method of an electrical connection structure according to the present invention is a method comprising the steps of: providing a carbon nanotube as an electrode; and contacting the electrode with a biopolymer.

A second aspect of the production method of an electrical connection structure according to the present invention is a method comprising, after the steps of providing the carbon nanotube as the electrode and contacting the electrode with the biopolymer, the step of applying an electric current between the electrode and the biopolymer.

A third aspect of the production method of an electrical connection structure according to the present invention is the method of the second aspect, wherein a voltage during application of the electric current is 1 to 20 V.

A fourth aspect of the production method of an electrical connection structure according to the present invention is the method of the first aspect, wherein the biopolymer is one of DNA and RNA.

A fifth aspect of the production method of an electrical connection structure according to the present invention is the method of the first aspect, wherein the biopolymer has a polar group, and the polar group and the electrode are made to contact each other.

A sixth aspect of the production method of an electrical connection structure according to the present invention is the method of the first aspect, wherein the electrode has a polar group at an end portion thereof, and the polar group and the biopolymer are made to contact each other.

A seventh aspect of the production method of an electrical connection structure according to the present invention is the method of the fifth aspect, wherein the polar group is selected from at least one of a carboxyl group, a carbonyl group, a hydroxyl group, an amine group, and an amide group.

A first aspect of the electrical connection structure according to the present invention is an electrical connection structure comprising at least an electrode formed by a carbon nanotube, and a biopolymer, wherein the electrode is in contact with the biopolymer.

A second aspect of the electrical connection structure according to the present invention is the electrical connection structure of the first aspect, wherein the biopolymer is one of DNA and RNA, and the electrode is in contact with a portion of the biopolymer where $Na^+$ ions on the surface of the one of DNA and RNA have been diffused.

A third aspect of the electrical connection structure according to the present invention is the electrical connection structure of the first aspect, wherein the electrode has a polar group at an end portion thereof and the biopolymer has a polar group at a portion thereof, the respective polar groups repelling each other, and the end portion of the electrode is in contact with a portion of the biopolymer other than the portion where the polar group is present.

A fourth aspect of the electrical connection structure according to the present invention is an electrical connection structure comprising at least an electrode formed by a carbon nanotube, and a biopolymer, wherein the electrode is in contact with the biopolymer via a polar group.

A fifth aspect of the electrical connection structure according to the present invention is the electrical connection structure of the fourth aspect, wherein the polar group is present at a surface of the biopolymer, and the biopolymer is a protein.

A sixth aspect of the electrical connection structure according to the present invention is the electrical connection structure of the fourth aspect, wherein the polar group is present at an end portion of the electrode.

A first aspect of the electrical wiring method according to the present invention is a method comprising the step of electrically connecting an electrode formed by a carbon nanotube to a biopolymer by making the electrode contact the biopolymer.

A second aspect of the electrical wiring method according to the present invention is the method of the first aspect, wherein, before electric properties of an electrical connection structure in which the biopolymer is electrically connected to the electrode are used, electric current is applied to the electrical connection structure in order to stabilize electrical connection between the biopolymer and the electrode.

A third aspect of the electrical wiring method according to the present invention is the method of the first aspect, wherein the electrode has a polar group at an end portion thereof, the polar group generating attraction force with respect to the biopolymer.

DESCRIPTION OF THE PREFERRED EMBODIMENTS

Figure 1:
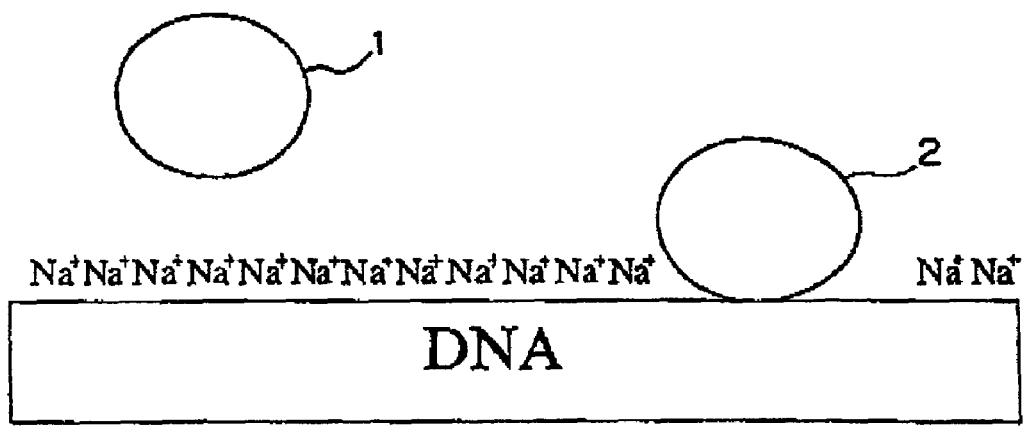
FIG. 1 is a conceptual view of DNA being contacted with a carbon nanotube. Each of reference numerals 1 and 2 denotes a carbon nanotube.

A production method of an electrical connection structure according to a first aspect of the present invention is a method in which a carbon nanotube is used as an electrode and the electrode is made to contact a biopolymer.

Further, a production method of an electrical connection structure according to a second aspect of the present invention is a method in which electric current is applied (electricity is turned on) between the electrode and the biopolymer after the electrode has been made to contact the biopolymer.

According to the above production methods of an electrical connection structure of the present invention, the carbon nanotube can be connected to the biopolymer in a stable manner.

The biopolymer described herein refers to a polymer present in a living body, such as DNA, RNA, or a protein. In recent years, artificial synthesis of DNA and proteins has become possible. Therefore, artificially made biopolymers can also be appropriately applied to the present invention. Further, the biopolymer may be formed by a combination of multiple types of biopolymers.

Moreover, the carbon nanotube (hereinafter referred to as a "nanotube" on occasion) is not particularly limited as long as the electric current is applied to the biopolymer via the carbon nanotube. A carbon nanotube having a single wall or multiple walls or modified carbon nanotubes (such as nano horn, nano beads, and nano coil) can be used, and a carbon nanotube having a diameter of 0.5 nm to 50 nm is preferably used. Further, a bundle of carbon nanotubes may also be used as long as they are electrically conductive.

According to the production methods of an electrical connection structure of the present invention, a stable contact state can be obtained by simply making the carbon nanotube contact the biopolymer, or by further applying the current to the carbon nanotube and the biopolymer after they have been made to contact each other for more stable connection. The principle of obtaining such a contact state is not clear but is thought to be due to the following actions.

The carbon nanotube is formed of a graphite structure sheet and has a structure of a hollow cylinder, closed at one end. Strong van der Waals' force is generated on the surface of the carbon nanotube. Therefore, when a chemically polar group (such as an OH group or a COOH group) or ion is present, a strong attraction force is generated. Further, since the graphite structure of carbon nanotube is stable, unlike a metal, the surface thereof is not easily oxidized, and the atomic arrangement on the surface is also stable.

In the biopolymer such as DNA or RNA, the surface of the DNA or RNA is stabilized by ion bonds to Na atoms. When Na is dissociated from the surface in water or the like because of chemical equilibrium, the surface takes on strong negative polarity. Three types of noncovalent bonds are present on the surface of a protein. Namely, ion bonds and hydrogen bonds which originate from an amino acid forming a polypeptide skeleton (for example, ion bonds between carboxyl groups and amine groups, and hydrogen bonds between carbonyl groups and amide groups) and van der Waals' force generated by the folded structure of the protein.

Accordingly, a large number of polar side chains are present on the surface of a polypeptide which forms a protein. Polar side chains are present on the surface of a molecule of an ordinary protein, thereby generating strong hydrogen bonds.

When the carbon nanotube is used as an electrode and made to contact (or connected to) a DNA or RNA molecule, or made to contact the molecule and then the current is applied thereto, $Na^+$ ions on the surface of the DNA or RNA molecule are diffused. As a result, stable contact between the DNA or RNA molecule and the carbon nanotube can be realized.

More specific description will be given with reference to FIG. 1. As a carbon nanotube 1 approaches the surface of DNA, ion bonds between the DNA surface and $Na^+$ ions become weak due to the effect of van der Waals' force of the carbon nanotube, and it becomes easy for the $Na^+$ ions to dissociate from the DNA. Then, by applying the voltage and the current to the carbon nanotube 1 and the DNA, the $Na^+$ ions are diffused into the inside of the DNA and the carbon nanotube, and, as can be seen by a carbon nanotube 2, the carbon nanotube is made to contact the DNA. Such contact is caused by an electrostatic attraction force acting between the clean surfaces of the carbon nanotube and the DNA, and therefore is very stable. This contact is realized by strong interaction between the carbon nanotube and the DNA surface.

In the case of an ordinary metal, such contact is impossible since an oxide film is present on the surface of the metal.

Even when DNA or RNA is merely made to contact the carbon nanotube, adherence is larger than that obtained when DNA or RNA is connected to a metal. Therefore, an electrical connection structure in which DNA or RNA is merely made to contact the carbon nanotube may also be used. In this case, when the current is applied to the carbon nanotube in order to utilize the electric properties of the biopolymer, the connection between the biopolymer and the carbon nanotube is further stabilized. Alternatively, by applying a current to the carbon nanotube before the electric properties of the biopolymer are put into practice, a more stable electrical connection between the biopolymer and the carbon nanotube of the electrical connection structure can be formed, and thereafter, the electrical connection structure can be subjected to actual use.

Moreover, when the current is applied to (or electricity is turned on for) the carbon nanotube and the biopolymer after the nanotube and the biopolymer are contacted with each other, electrical interaction between them becomes larger and a more stable contact state can be obtained. The current to be applied is preferably 0.1 to 100 nA, and more preferably 5 to 50 nA.

When the protein and the carbon nanotube are made to contact each other, a strong attraction force is generated between a polar group on the surface of the protein molecule and the carbon nanotube. Accordingly, as described above, a stable electrical connection can be realized by the mere contact of the protein and the carbon nanotube.

Further, when a polar group, for example, a carboxyl group, which causes an attraction force between the biopolymer such as a protein, DNA, or RNA, is added to the carbon nanotube by subjecting an open end (end portion) of the carbon nanotube to chemical treatment with an acid (such as nitric acid, sulfuric acid, or a mixture thereof), strong polarities are generated only at the end portion, and selective electrical connections to the biopolymers are made possible. Namely, in order to connect the carbon nanotube to a predetermined portion of molecules forming the biopolymer, it suffices that a polar group which generates an attraction force to the macromolecule forming the portion is linked to the end portion of the carbon nanotube. Conversely, when connection of the end portion of the carbon nanotube to a predetermined portion of the biopolymer is not desired, by linking to the end portion of the carbon nanotube a group whose polarity repels the molecule forming the predetermined portion, connection of the predetermined portion to the end portion of the carbon nanotube can be prevented, and the predetermined portion can be connected to the carbon nanotube at a side thereof.

The end portion described herein refers to, of a carbon nanotube having a length L, an area extending from a tip to 0.1×L (preferably 0.01×L).

As described above, since the carbon nanotube and the biopolymer are stably connected to each other, a stable contact resistance can be realized.

Since the electrical connection structure is simple and minute in that the carbon nanotube is used as the electrode and the electrode contacts the biopolymer, nanometer-scale electrical wiring is possible. Even when, for example, a biopolymer which is an insulator having a resistance of 5 MΩ·cm or more is used, the biopolymer can be used as an electric element, and electrical properties of the biopolymer can be used. Specific examples of electric elements include rectifiers, transistors, switching elements, integrated circuits, solar batteries, optical sensors, chemical substance-functional sensors, and the like.

Moreover, if electrical wiring is carried out using the principle of the above electrical connection structure, namely, if the electrical wiring method in which electrical connection is carried out by bringing the electrode into contact with the biopolymer is used, stable electrical wiring to the biopolymer such as DNA, RNA, or a protein is made possible and can be widely used in the electronic industry for semiconductor devices and the like.

The production method of the electrical connection structure according to the present invention will be hereinafter described by way of a preferable embodiment.

When natural DNA or RNA is used as the biopolymer, purification thereof needs to be carried out since DNA and RNA contain impurities such as proteins.

For example, purification of the DNA is preferably carried out as follows. First, proteins, which are an impurity, are removed by using alcohols such as methanol and ethanol, or ethers such as methyl ether and ethyl ether. Thereafter, the DNA is washed two or three times with a buffer solution (containing 300 mM of sodium chloride, 10 mM of sodium carbonate, and 5 mM of EDTA) to remove impurities. When DNA of a higher purity is desired, the DNA is preferably isolated by electrophoresis. After the washing with the buffer solution, the DNA is filtered and dispersed in, for example, a mixed solution of ethanol and water (ethanol: 20%, water: 80%) in order to remove salts. It is preferable to use ethanol which is, after distillation thereof, filtered with a filter having a pore diameter of 0.1 μm, and ultrapure water (having a resistance value of $10^{18}\Omega$ or more). Removal of salts is carried out two or three times with the mixed solution of ethanol and water to adjust the concentration of the DNA or RNA to 0.01 to 0.1% by mass. During the process of removing impurities, DNA (or RNA) molecules are likely to be cohesive and form spherical bodies. Thus, the DNA is held in the mixed solution of ethanol and water for one to ten days to separate the molecules. The temperature during this process is preferably 2 to 10° C. In general, when DNA is held in the mixed solution at 7° C., it takes seven days for the DNA molecules to separate into a fibrous form.

RNA can also be purified in a similar manner.

Proteins, on the other hand, have molecules of various shapes and sizes. Thus, in general, proteins are preferably separated and purified by chromatography. In the present embodiment, it is preferable to form a column for chromatography using a combination of the principles of ion exchange chromatography, gel filtration chromatography, and affinity chromatography, and to separate proteins according to the purpose. Subsequently, by separating proteins by one-dimensional polyacrylamide gel electrophoresis, the degree of purification of proteins can be determined according to the purpose. Further, separations and purifications of proteins are preferably carried out by two-dimensional polyacrylamide gel electrophoresis.

The carbon nanotube which is used as a material for an electrode is produced by an arc discharge method or laser ablation method. Two types of carbon nanotubes are mainly used those having a single wall and those having multiple walls. The carbon nanotube having a single wall has a diameter of 0.5 nm to 3 nm, while the carbon nanotube having multiple walls has a diameter of 5 nm to 20 nm.

Next, a method of making DNA or RNA and a carbon nanotube contact each other will be described.

First, an insulating substrate (such as silicon oxide, sapphire, or mica), which has an electrical resistance higher than that of the biopolymer, such as DNA, RNA, or proteins (hereinafter referred to as a "sample") is prepared, and a molecule of the sample which has been separated in the mixed solution is fixed onto the substrate.

Subsequently, two or more carbon nanotubes serving as electrodes are placed onto the molecule of the sample by an arbitrary method. The distance between the carbon nanotubes serving as the electrodes on the sample molecule is preferably 1 nm to 50 nm while each of the carbon nanotubes maintains an electrically independent state. Next, voltage is applied between the carbon nanotubes, and the sample molecule and the carbon nanotubes serving as the electrodes are fixed so that they are electrically connected to each other. At this time, the voltage to be applied between the carbon nanotubes serving as the electrodes is preferably 1 V to 20 V. The current applied to the carbon nanotubes serving as the electrodes and the sample is preferably 0.1 nA to 100 nA.

An example of a method of operating the carbon nanotubes and thereby connecting them to an arbitrary portion of the sample molecule is a method in which an atomic force microscope (hereinafter referred to as an "AFM") is used. The AFM is a measuring device which measures, when a sharp probe mounted to a cantilever scans the surface of a sample, the amount of deflection of the cantilever by using an optical lever method, which amount is obtained corresponding to the irregularities of the sample surface, such that an image of the irregularities of the sample is obtained. However, since an ordinary AFM has only one probe, a multi-probe AFM having three or more probes is preferably used.

Figure 2:
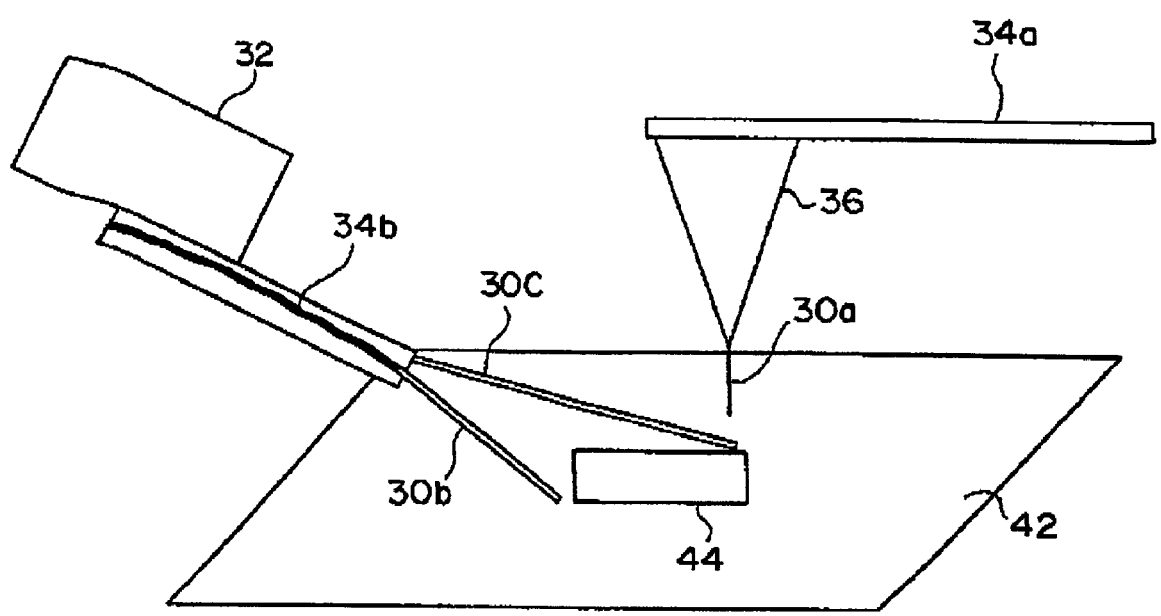
FIG. 2 is a conceptual view of a multi-probe atomic force microscope. Each of reference numerals 30a, 30b, and 30c denotes a carbon nanotube probe, reference numeral 32 denotes a piezoactuator, each of reference numerals 34a and 34b denotes a probe support, reference numeral 42 denotes a substrate, and reference numeral 44 denotes a sample.

One example of the multi-probe AFM which can operate the carbon nanotubes and apply the electric current thereto is shown in FIG. 2.

Three probes are used in the multi-probe AFM. Further, one of the three probes, namely, a carbon nanotube probe 30a, is used for the atomic force microscope (AFM). The carbon nanotube probe 30a is fixed to the tip of a scanning portion 36, which is formed in a pyramidal shape and supported by a probe support 34a. Further, another two carbon nanotube probes 30b and 30c are fixed to an end of a probe support 34b so as to form a substantially inverted "V" shape and are electrically independent from each other. The probe support 34b is joined to a piezoactuator 32 and structured so as to be freely movable in three dimensions. A sample 44 is placed on a substrate 42.

In order to use the multi-probe AFM to make the carbon nanotubes contact the biopolymer such as DNA, it is preferable to carry out the following process.

First, the position of a target molecule of DNA is observed and specified by the multi-probe AFM. Next, one carbon nanotube serving as an electrode is made to transversely contact the DNA molecule while being moved by the multi-probe AFM. Similarly, another carbon nanotube is disposed so as to be spaced a predetermined distance from the one carbon nanotube and is made to transversely contact the DNA molecule. Similar operations are repeated as needed.

Moreover, the carbon nanotube serving as the electrode is placed in a mixed solution of nitric acid and sulfuric acid (nitric acid (68% solution): sulfuric acid (96% solution)=3: 1) in a concentration of 0.1% by weight, and ultrasonic vibration is carried out for two hours. As a result, a carboxyl group is attached to both ends of the carbon nanotube. When this carbon nanotube is used as the electrodes depending on the polarity of the sample, the carbon nanotube can be selectively connected to the sample at the end of the carbon nanotube.

EXAMPLES

Examples of the present invention will now be described. However, the present invention is not limited to these Examples.

Example 1

DNA separated from a sperm of a wild salmon was used.

In order to remove impurities such as proteins, 10 mg of the DNA was dispersed in 100 ml of ethanol (99.9%). The dispersion was stirred at room temperature for 30 minutes and filtered by using a PTFE filter having a pore diameter of 1 μm. This process was repeated three times. Subsequently, the DNA whose proteins had been removed was dispersed in 100 ml of a buffer solution (containing 300 mM of sodium chloride, 10 mM of sodium carbonate, and 5 mM of EDTA). Ultrapure water (having a resistance value of 18 MΩ or more) was used as the water of the solution. The dispersion was stirred at room temperature for 30 minutes and filtered by using a PTFE filter having a pore diameter of 1 μm to remove impurities. Finally, in order to remove salts, the DNA was dispersed in a mixed solution of ethanol and water (ethanol: 20%, water; 80%). Ethanol which had been filtered after distillation thereof with a filter having a pore diameter of 0.1 μm and ultrapure water (having a resistance value of 18 MΩ or more and sterilized with ultraviolet light) were used in the solution.

After dispersion, the resulting dispersion was subjected to shaking for 10 minutes and then separation by a centrifuge separation method (rotation speed: 300 rpm, rotating time: one hour). This process was carried out three times, and the concentration of the DNA was ultimately adjusted to 0.02%.

Thereafter, a DNA molecule was placed on a substrate made of silicon oxide, and two carbon nanotubes serving as electrodes were made to contact the DNA molecule by a multi-probe AFM. The interval between the two carbon nanotubes was 20 nm.

As the above carbon nanotubes, carbon nanotubes each having a single wall obtained by arc discharge were used.

Figure 3:
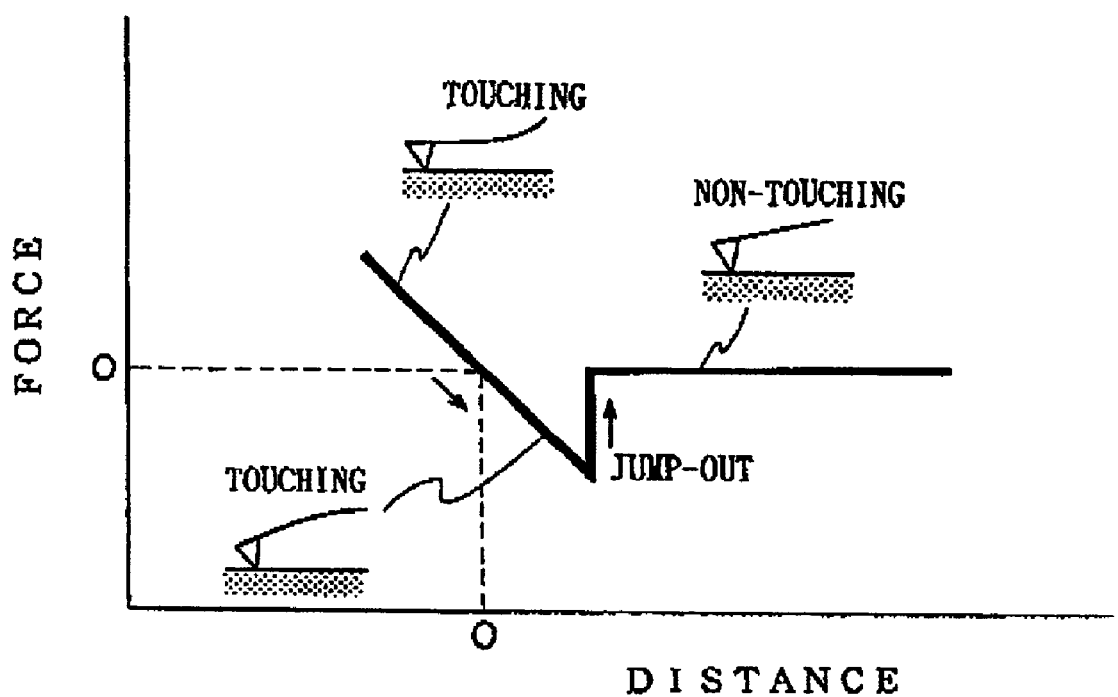
FIG. 3 is an explanatory view showing the principle of adherence measurement.

In the above-described state, a difference in adherence between the DNA molecule and the carbon nanotubes was observed. The principle of measurement of adherence is shown in FIG. 3. Adherence refers to the force acting when the cantilever of the AFM is made to contact the sample and then pulled up.

Namely, an amount designated "JUMP-OUT" in FIG. 3 refers to adherence. Accordingly, by using gold and a carbon nanotube as probes and comparing their respective amounts of adherence to the DNA, a dynamic connection of the electrodes can be measured.

Figure 4:
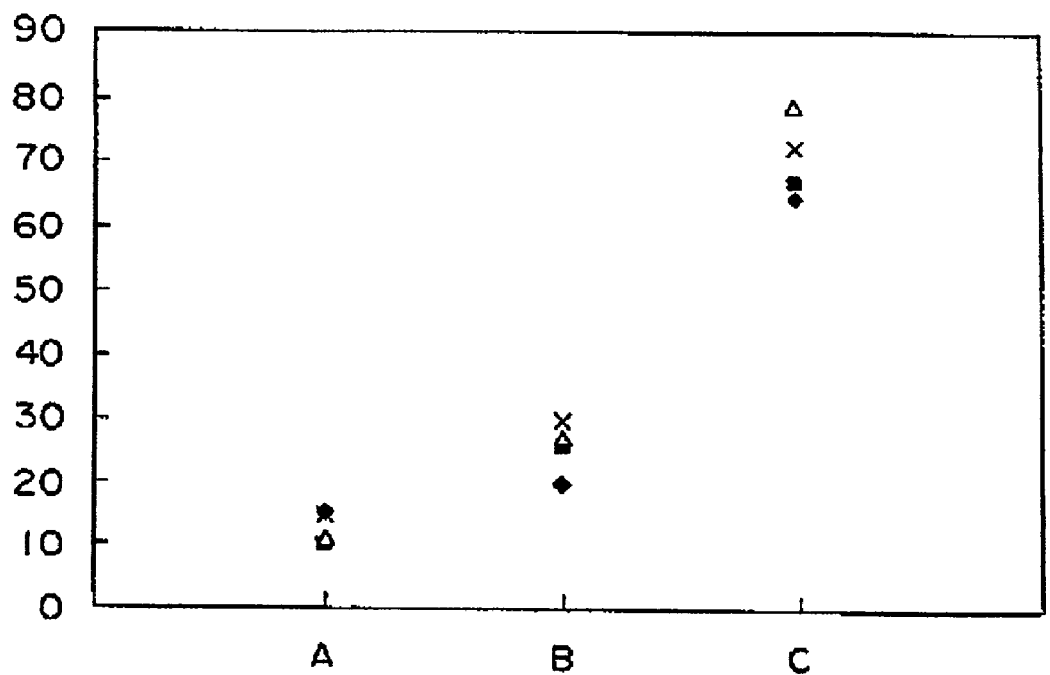
FIG. 4 is a view showing changes in adherence caused by probes.

By using the DNA as the sample and using gold and a carbon nanotube as the probes, measurement of changes in the amount of adherence was carried out, four times for each probe. The results are shown in FIG. 4. When the probe was gold, the adherence was 10 nN to 15 nN. However, when the probe was the carbon nanotube, the adherence was 20 nN to 30 nN. Further, when a voltage of 15 V was applied to the carbon nanotube, the adherence between the carbon nanotube and the DNA was increased to a range of 65 nN to 80 nN.

From the above results, it was proved that a dynamic connection between the carbon nanotube and the DNA molecule was stronger than that between the DNA molecule and a metal such as gold, and that the carbon nanotube was a material preferable for electric wiring to the DNA molecule.

Example 2

Two carbon nanotubes were connected to DNA similarly to Example 1, and changes in adherence before and after application of voltage and changes in electric resistance were measured in the same way as in Example 1. When the electrode width of the carbon nanotubes on a single DNA molecule was 30 nm, changes in electric resistance before and after application of a voltage of 15 V were measured. The bias voltage was 0.2 V. Before the voltage of 15 V was applied, the current was 15 pA to 30 pA. However, after the voltage of 15 V had been applied, the current was 80 pA. Further, before the voltage of 15 V was applied, the current had a fluctuation of 10 pA to 15 pA. However, the fluctuation of the current was decreased to 5 pA or less after the voltage of 15 V had been applied. Moreover, since a current leakage on the substrate was 3 pA to 4 pA, the fluctuation of the current value at a position where the carbon nanotubes and the DNA molecule contacted each other after the voltage of 15 V had been applied was determined to be 1 pA or less.

From the above results, it was proved that making the carbon nanotubes and the DNA molecule contact each other was effective for electric wiring.

Example 3

Two carbon nanotubes (each having multiple walls) were connected to DNA similarly to Example 1, and current/voltage characteristics before and after application of voltage were compared. For comparing current/voltage characteristics, the two carbon nanotubes were used as a source electrode and a drain electrode, and a carbon nanotube having a single wall was used as a gate electrode The width of the source electrode and the drain electrode was 8 nm, and the width of the gate electrode was 1.5 nm. Further, a substrate formed of silicon oxide was used.

Figure 5:
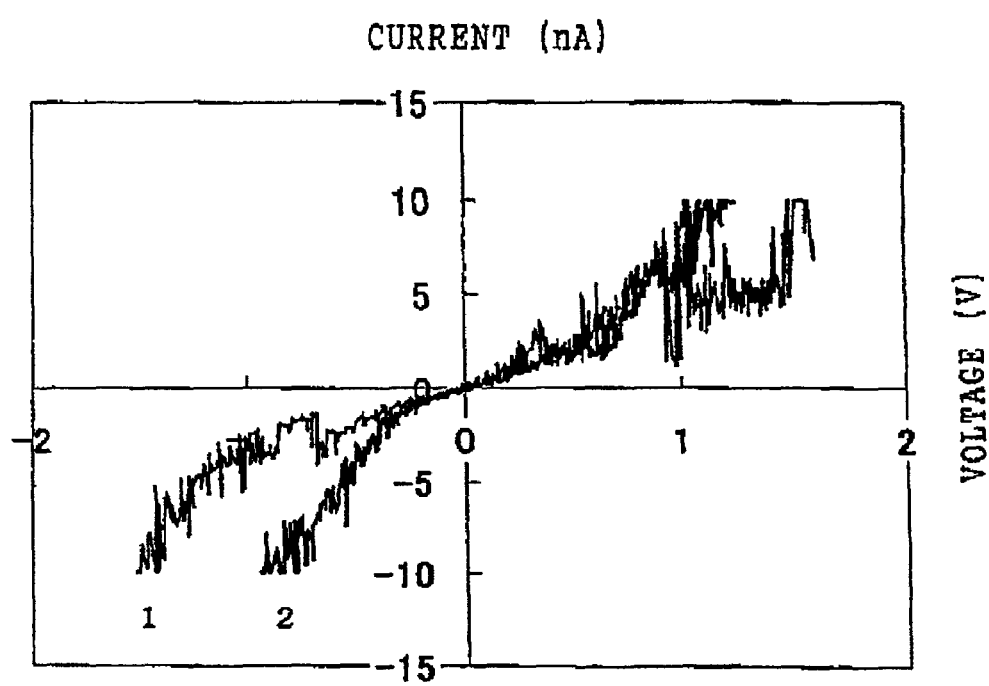
FIG. 5 illustrates current/voltage characteristics of Example 3.

In practice, when the electrode width of the carbon nanotube on a single DNA molecule was 20 nm, current/voltage characteristics before and after application of a voltage of 15 V were measured. The results are given in FIG. 5. The current/voltage characteristics became stable after the voltage had been applied. From this fact, it was proved that carbon nanotubes used in electric wiring to DNA arc useful for electronic devices such as transistors.

Example 4

A carbon nanotube to be used as an electrode was placed in a mixed solution of nitric acid and sulfuric acid (nitric acid (68% solution): sulfuric acid (96% solution)=3:1) in a concentration of 0.01% by weight, and the mixture was subjected to ultrasonic vibration for two hours. As a result, a carboxyl group was attached to both ends of the carbon nanotube. (The carbon nanotube had a length of 120 nm, and the end regions were from the edge to from 1 nm from the edge.) The carbon nanotubes thus formed were used as electrodes and made to contact a protein (globulin) molecule. Then, a difference in adherence between the protein molecule and the carbon nanotubes with and without carboxyl groups attached thereto was measured.

When no carboxyl groups were attached to the ends of the carbon nanotube, the adherence was 38 nN to 45 nN. However, when the carbon nanotube having carboxyl groups attached thereto was used, the adherence increased to a range of 80 nN to 120 nN.

When a metal electrode and globulin were made to contact each other, there was little adherence: they were merely in contact with each other.

Accordingly, it was proved that, by attaching carboxyl groups to the ends of the carbon nanotube, dynamic connection was selectively increased, and that the carbon nanotube having carboxyl groups attached thereto is a material preferable for electric wiring to a protein.

As described above, in accordance with the present invention, it is possible to provide an electrical connection structure which efficiently connect electric wiring to a biopolymer such as DNA, RNA, or proteins, a production method of the electrical connection structure, and an electric wiring method which enables nanometer-scale electric wiring.

What is claimed is:

1. A production method of an electrical connection structure, the method comprising the steps of:
    operating at least one carbon nanotube as an electrode to an arbitrary portion of a biopolymer; and
    contacting the electrode with the biopolymer at the arbitrary portion;
    wherein the electrode and the biopolymer are fixed together in a stable electrically connected state by the contacting step.

2. The method of claim 1, further comprising, after the steps of providing the carbon nanotube as the electrode and contacting the electrode with the biopolymer, the step of applying a voltage between the electrode and the biopolymer.

3. The method of claim 2, wherein the step of applying a voltage between the electrode and the biopolymer comprises applying a voltage of 1 to 20 volts.

4. The method of claim 1, wherein the biopolymer is one of DNA and RNA.

5. The method of claim 1, wherein the biopolymer has a polar group, and the polar group and the electrode are made to contact each other.

6. The method of claim 1, wherein the electrode has a polar group at an end portion thereof, and the polar group and the biopolymer are made to contact each other.

7. The method of claim 5, wherein the polar group is selected from at least one of a carboxyl group, a carbonyl group, a hydroxyl group, an amine group, and an amide group.

8. An electric wiring method, comprising the step of operating and electrically connecting at least one carbon nanotube as an electrode to a biopolymer, wherein the electrode and the biopolymer are fixed together at an arbitrary portion of the biopolymer in a stable electrically connected state.

9. The electric wiring method of claim 8, wherein an electric current is applied to the electrode and the biopolymer in a stable electrically connected state in order to stabilize electrical connection between the biopolymer and the electrode.

10. The electric wiring method of claim 8, wherein the electrode has a polar group at an end portion thereof, the polar group generating attraction force with respect to the biopolymer.

11. A production method of an electrical connection structure, the method comprising the steps of:
    operating at least one carbon nanotube as an electrode to an arbitrary portion of a biopolymer; and
    contacting the electrode with the biopolymer at the arbitrary portion;
    wherein the electrode and the biopolymer are fixed together in a stable electrically connected state by the contacting step, and wherein contacting the electrode with the biopolymer comprises synthesizing the biopolymer onto the carbon nanotube.

12. The production method of claim 1, wherein the biopolymer is a natural biopolymer.

13. The production method of claim 1, wherein the biopolymer is an artificially synthesized biopolymer.

14. A production method of a semiconductor device including an electrical connection structure, the method comprising the steps of:

operating at least one carbon nanotube as an electrode with the biopolymer at the arbitrary portion;

contacting the electrode with the biopolymer at the arbitrary portion;

wherein the electrode and the biopolymer are fixed together in a stable electrically connected state by the contacting step.

* * * * *